United States Patent [19]

Yamamoto et al.

[11] Patent Number: 4,918,068
[45] Date of Patent: * Apr. 17, 1990

[54] CEPHEM COMPOUNDS

[75] Inventors: Yuichi Yamamoto, Yokohama; Kunio Atsumi; Kenji Sakagami, both of Kawasaki; Takashi Yoshida, Tokyo; Ken Nishihata; Sinichi Kondo, both of Yokohama, all of Japan

[73] Assignee: Meiji Seika Kaisha, Ltd., Tokyo, Japan

[ * ] Notice: The portion of the term of this patent subsequent to Jun. 13, 2006 has been disclaimed.

[21] Appl. No.: 19,172

[22] Filed: Feb. 26, 1987

[30] Foreign Application Priority Data

Mar. 3, 1986 [JP] Japan .................. 61-44203

[51] Int. Cl.$^4$ .................. C07D 501/24; A61K 31/545
[52] U.S. Cl. .................. 514/206; 540/227; 540/222
[58] Field of Search .................. 540/227; 514/206, 202

[56] References Cited

U.S. PATENT DOCUMENTS 4,546,101 10/1985 Takaya et al. .................. 540/224 X
4,839,350 6/1989 Atsumi et al. .................. 540/222

FOREIGN PATENT DOCUMENTS 0103264 3/1984 European Pat. Off. .
0175610 3/1986 European Pat. Off. .

OTHER PUBLICATIONS

Patent Abstracts of Japan, vol. 11, No. 200, Jun. 27, 1987, "Novel Cephem Compound".
Atsumi, et al., Chem. Abstracts vol. 106 (1987) entry 67001b.

Primary Examiner—Nicholas S. Rizzo
Attorney, Agent, or Firm—Larson and Taylor

[57] ABSTRACT

There are provided new cephem compounds (synisomers) represented by the following general formula (I):

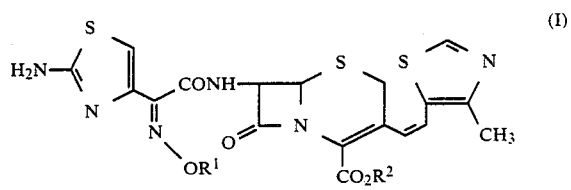

wherein $R^1$ means a lower group, $R^2$ denotes an ester-forming group of the carboxyl group, and the 4-methylthiazolyl group and the cephem moiety are cis to each other relative to the carbon-carbon double bond of the substituted vinyl group in the side chain at the 3-position of the cephem nucleus. The cephem compounds exhibit strong antibacterial activities not only against resistant strains of bacteria and gram-negative bacteria but also against gram-positive bacteria and moreover have very low toxicity.

9 Claims, No Drawings

CEPHEM COMPOUNDS

SUMMARY OF THE INVENTION

This invention relates to novel esters of cephem compounds, and more specifically to orally-administrable novel esters of cephem compounds, which have excellent oral absorption.

BACKGROUND OF THE INVENTION

Some cephalosporin compounds which bearing an α-(substituted imino)-α-(2-aminothiazolyl)-acetyl group as a side chain at the 7-position and a β-substituted vinyl group as a side chain at the 3-position of the cephem nucleus are known, as disclosed in Japanese Patent Application first publication "Kokai" Nos. 124790/80, 122383/81 and 76088/84, U.K. patent application first publication No. 2128990A and U.S. Pat. No. 4,307,116.

Cephalosporin-type antibiotics are known to be highly and broadly active against a variety of gram-positive and gram-negative bacteria. Various kinds of semi-synthesized cephalosporin compounds have already been available commercially and applied clinically for the therapeutic treatment of various infections diseases. But, only a very few ones amongst these semi-synthesized cepahlosporin compounds are practically effective against the strains of bacteria of the genus Pseudomonas and Protéus. These known cepahlosporin compounds are also degradable by a β-lactamase which is produced by some resistant strains of bacteria, and they exhibit only a poor activity against some resistant strains of bacteria which have now been a target of clinical treatments of bacterial infections (see: W. E. Wick "Cephalosporins and Penicillins, Chemistry and Biology", edited by E. H. Flynn, Academic Press, New York, N.Y., 1972, Chapter 11.)

We, the present inventors, have already provided a new cephalosporin compound of the general formula

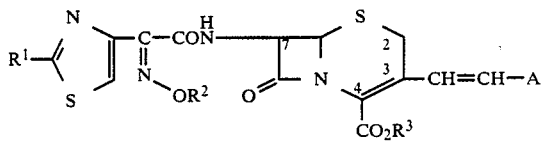

wherein $R^1$ is an amino group or a protected amino group; $R^2$ is a lower alkyl group, a carboxymethyl group or a protected carboxymethyl group; $R^3$ is a hydrogen atom, a salt-forming cation or a carboxyl-protecting group; A is an unsubstituted or substituted phenyl group, an unsubstituted or substituted furyl group, an unsubstituted or substituted thiazolyl group or an unsubstituted or substituted 3-lower-alkylthiazolio group, and a pharmaceutically acceptable salt or ester of said cephalosporin compound (see pending U.S. patent application Ser. No. 769,746 and European patent application No. 85 401741.5).

As described above, the cephem antibiotics exhibit strong antibacterial activities against gram-positive and gram-negative bacteria and have low toxicity. Accordingly, they are now employed widely as therapeutic agents for various bacterium-related infections diseases.

Some new problems have, however, arisen such that more resistant strains of bacteria have occurred due to the wide use of the cephem antibiotics, and the recently-developed cephem antibiotics of so-called "third generation" do not show fully strong antibacterial activities against gram-positive bacteria, although their antibacterial activities are high against gram-negative bacteria and resistant strains or bacteria [for example, "Antimicrobial Agents and Chemotherapy" 25, 98 (1984)]. In addition, many of the conventional drugs of cephem type have been developed as parenteral solutions. They are hence accompanied by a serious drawback that their absorpability in living animals are too low to show sufficient effectiveness when administered orally.

DETAILED DESCRIPTION OF THE INVENTION

When a view to provide new cephem compounds which are free from the above problems, we, the present inventors, have further synthesized a number of cephem compounds and investigated their antibacterial activities and oral absorpability, etc. As a result, it has now been found that new compounds of the general formula (I) given below are absorbable well through the digestive tubes of animal upon oral administration, leading to completion of this invention.

In one aspect of this invention, therefore, there is provided the syn-isomer of a cephem compound represented by the following general formula (I):

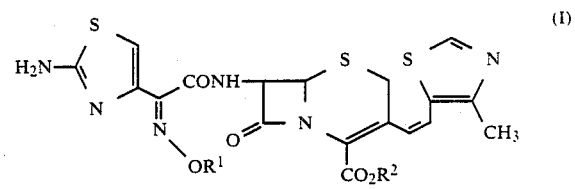

wherein $R^1$ means a lower alkyl group, $R^2$ denotes an ester-forming group of the carboxyl group, and the 4-methylthiazolyl group and the cephem moiety are cis to each other relative to the carbon-carbon double bond of the substituted vinyl group in the side chain at the 3-position of the cephem nucleus.

When the compound (I) of this invention is administered orally, the ester moiety of the compound is hydrolyzed by an enzyme in the body subsequent to its prompt absorption through the digestive tubes. The cephem compound thus formed in the form of a free carboxylic acid exhibits strong antibacterial activities not only against resistant strains of bacteria and gram-negative bacteria but also against gram-positive bacteria and moreover has very low toxicity. The compound (I) of this invention can therefore be used, by its oral administration, for the treatment of various infections diseases caused by pathogenic bacteria and is thus very useful as a medicine.

The above and other objects, features and advantages of the present invention will become apparent from the following description and the appended claims.

The compound represented by the general formula (I) in its broadest scope includes both cis-isomer and trans-isomer. In the cis-isomer of the compound (I), the substituent, i.e., the 4-methylthiazolyl group and the cephem moiety are cis to each other relative to the carbon-carbon double bond of the substituted vinyl group in the side chain at the 3-position of the cephem nucleus. The 4-methylthiazolyl group may also be trans to the cephem moiety in the trans-isomer. The compound of this invention is limited to the cis-isomer.

The term "lower alkyl group" as used herein for the group $R^1$ in the compound of this invention means an alkyl group having 1-6 carbon atoms, with a methyl or ethyl group being preferred. The ester-forming group $R^2$ of the carboxyl group may be any ester-forming group so long as the resultant ester moiety is hydrolyzable in the body after an oral administration of the compound. Illustrative examples of the ester-forming group may include lower alkanoyloxyalkyl groups such as acetoxymethyl, 1-acetoxyethyl and pivaloyloxymethyl groups, lower alkoxycarbonyloxyalkyl groups such as 1-(ethoxycarbonyloxy) ethyl group, phthalidyl group and (5-methyl-2-oxo-1,3-dioxolen-4-yl)-methyl group, etc.

Preferred examples of the new compound of the formula (I) according to this invention are listed below:

(1) Pivaloyloxymethyl 7-[2-ethoxyimino-2-(2-aminothiazol-4-yl)acetamido]-3-[2-(4-methylthiazol-5-yl)vinyl]-3-cephem-4-carboxylate.

(2) Acetoxymethyl 7-[2-methoxyimino-2-(2-aminothiazol-4-yl)acetamido]-3-[2-(4-methylthiazol-5-yl)vinyl]-3-cephem-4-carboxylate.

(3) 1-Acetoxyethyl 7-[2-methoxyimino-2-(2-aminothiazol-4-yl)acetamido]-3-[2-(4-methylthiazol-5-yl)vinyl]-3-cephem-4-carboxylate.

(4) 1-Ethoxycarbonyloxyethyl 7-[2-methoxyimino-2(2-aminothiazol-4-yl)acetamido]-3-[2-(4-methylthiazol-5-yl)-vinyl]-3-cephem-4-carboxylate.

(5) Phthalidyl 7-[2-methoxyimino-2-(2-aminothiazol-4-yl)acetamido]-3-[2-(4-methylthiazol-5-yl)vinyl]-3-cephem-4-carboxylate.

(6) (5-Methyl-2-oxo-1,3-dioxolen-4-yl)methyl 7-[2-methoxyimino-2-(2-aminothiazol-4-yl)-acetamido]-3-[2-(4-methylthiazol-5 yl)vinyl]-3-cephem-4-carboxylate. 2-(4-methylthiazol-5-yl)vinyl]-3-cephem-4-carboxylate.

Description will next be made of the preparation of the compound of this invention. Namely, the compound of the general formula (I) is prepared by reacting a compound of the following formula (II):

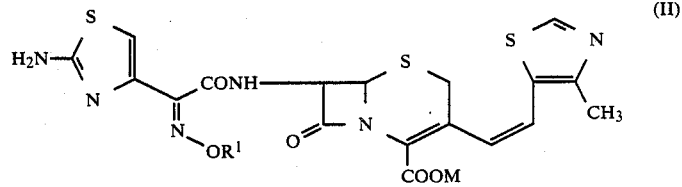

(II)

wherein $R^1$ has the same meaning as defined above and M denotes a cation forming a salt with the carboxyl group, with a compound of the following general formula (III):

$R^2-X$                (III)

wherein $R^2$ has the same meaning as defined above and X stands for a leaving group or atom.

As illustrative examples of the salt formed from the carboxyl group and the cation M in the compound (II) may be mentioned metal salts, including alkali metal salts such as sodium salt and potassium salt and alkaline earth metal salts such as calcium salt; and organic amine salts and ammonium salts such as triethylamine salt, tetrabutylammonium salt and dicyclohexylamine salt. Of these, the sodium salt, potassium salt, triethylamine salt and the like are preferred.

Illustrative examples of the leaving group or atom X in the compound (III) may include halogen atoms such as chlorine atom, bromine atom and iodine atom, arylsulfonyloxy groups such as toluenesulfonyloxy group, lower alkanesulfonyloxy groups such as methanesulfonyloxy group, etc. Among these, a bromine or iodine atom is preferred. The kind of the leaving group or atom is suitably chosen in view of the preparation processes of the starting compounds and the readiness of the reaction.

Upon conducting the esterification reaction between the compound (II) and the compound (III), N,N-dimethylformamide, dimethylsulfoxide, acetonitrile, acetone or the like is generally used as a reaction solvent. No particular limitation is imposed on the reaction temperature. Namely, the reaction is carried out usually under cooling or heating. It is preferable to conduct the reaction around 0° C. Purification of the reaction product may be carried out subsequent to the completion of the reaction, and, for instance, a pure product of the intended compound (I) can be obtained by subjecting the reaction product to a post treatment in a manner known per se in the art and if necessary, purifying it further by one or more of various chromatographic techniques and/or recrystallization.

When the compound (I) of this invention is administered for therapeutic purposes, the compound (I) may be formulated into a preparation form suitable for oral administration such as capsules, tablets or dry syrup according to a method practiced routinely in the art by optional addition of various additives such as excipient, binder, and lubricant.

Rates of recovery of some of the compound (I) of this invention in urine upon their oral administration will next be demonstrated. A higher rate of recovery of a test compound in urine indicates that the test compound as orally administered has been absorbed well through the digestive tube and then excreted without degradation in vivo. Subsequent to the absorption of the compound (I) in the body, the ester moiety of each compound (I) of this invention is hydrolyzed by an esterase present in the body. The resultant cephem compound in the form of a free carboxylic acid exhibits antibacterial activities. It is therefore possible to determine the rate of recovery of each test compound in urine by measuring the concentration of the corresponding free acid remaining in urine.

Test 1:

Measurement of rates of recovery in urine

Testing method:

To mice (ICR-strain, male, 4 weeks of age) was orally administered a test compound at a dosage of 0.5 mg per mouse. The test compound was given as a suspension of 0.2% carboxymethylcellulose (CMC) in water. Until the end of the 4th hour after the administration, urine was collected together from three of the mice and its total amount was measured precisely. A portion of the urine was then diluted with sterilized water to prepare fivefold and 25-fold dilute solutions as test solutions, respectively.

Quantitative assay:

The concentration of the cephem compound contained in the form of a free acid in each test solution was quantitatively assayed by the paper disk assay method in which Escherichia coli K-128236 was used as an assaying strain.

Test Compound:

1-Acetoxyethyl 7-[2-methoxyimino-2-(2-aminothiazol-4-yl)acetamido]-3-[2-(4-methylthiazol-5-yl)vinyl]-3-cephem-4-carboxylate (syn-isomer, cis-isomer) (Compound A).

Pivaloyloxymethyl 7-[2-ethoxyimino-2-(2-aminothiazol-4-yl)acetamido]-3-[2-(4-methylthiazol-5-yl)vinyl-]-3-cephem-4-carboxylate (syn-isomer, cis-isomer) (Compound B).

Test results are shown in the following table.

| Test compound | Rate of recovery in urine* until the end of the 4th hour |
| --- | --- |
| Compound A | 14% |
| Compound B | 20% |

*Recovery rate of the free acid as formed by the hydrolysis of the ester moiety.

Incidentally, the compound of the general formula (II) employed as a raw material in the preparation of the compound (I) of this invention is a novel compound. It may be prepared by the following process, namely, by reacting a compound represented by the following general formula (IV):

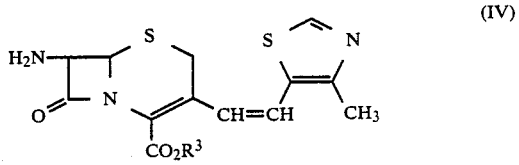

in which $R^3$ means an ester-forming group such as diphenylmethyl group, a reactive derivative thereof at the amino group or a salt thereof, with a compound represented by the following general formula (V):

wherein R is a protected amino group and $R^1$ has the same meaning as defined above, a reactive derivative thereof at the carboxyl group or a salt thereof and then by interchanging the ester-forming group of the 2-carboxyl group of the resultant condensation product with a cation M by a saponification reaction.

The reactive derivative of the compound of the formula (IV) can be suitably selected in accordance with the kind of the reactant compound (V) to be employed.

The condensation reaction between the compound (IV) and the compound (V) is conducted usually in a conventional solvent such as water, acetone, dioxane, acetonitrile, chloroform, methylene chloride, ethylene chloride, tetrahydrofuran, ethyl acetate, N,N-dimethylformamide or pyridine or in another organic solvent which does not give any adverse influence to the above reaction. These solvents may also be employed as mixtures with water.

When the compound (V) is used in its free acid or salt form in the above condensation reaction, it is desirable to conduct the reaction in the presence of a condensing agent. As an exemplary condensing agent may be mentioned N,N'-dicyclohexylcarbodiimide and N-cyclohexyl-N'-morpholinoethylcarbodiimide, as well as such agent which are obtained by a reaction between N,N-dimethylformamide and thionyl chloride, phosgene, phosphorus oxychloride or the like, namely, so-called Vilsmeier's reagent; or the like.

The above condensation reaction may also be conducted in the presence of an inorganic base or organic base. Illustrative examples of such an inorganic base or organic base include alkali metal hydrogen carbonates such as sodium hydrogen carbonate and potassium hydrogen carbonate, alkali metal carbonates such as sodium carbonate and potassium carbonate, alkaline earth metal carbonates such as calcium carbonate, and tri(-lower)alkylamines such as trimethylamine.

No particular limitation is imposed on the reaction temperature. The reaction is conducted usually under cooling or heating.

In the compound (II) which has been obtained through the above-described reaction, the carboxyl-protecting group and/or amino-protecting group may be removed by methods known per se in the art. For the removal of the carboxyl-protecting group and/or amino-protecting group, suitable methods may be chosen in accordance with the kinds of the protecting groups to be removed. For the removal of the amino-protecting group, any conventional deprotecting method such as hydrolysis or reduction may be applied. Hydrolysis with an acid is one of the common deprotecting methods. Acidic hydrolysis may be applied to for the removal of an amino-protecting group, such as an alkoxycarbonyl, formyl or trityl group. As an exemplary acid useful for this hydrolysis, an organic and inorganic acid such as formic acid, trifluoroacetic acid, p-toluenesulfonic acid or hydrochloric acid, preferably, formic acid, trifluoroacetic acid, hydrochloric acid or the like which facilitates the post treatment, may be chosen suitably in accordance with the kind of the amino-protecting group. The hydrolyzing reaction to this end may be conducted either in the absence of any solvent or in the presence of water, a hydrophilic organic solvent or a mixed solvent thereof. When trifluoroacetic acid is used, the reaction for the acidic hydrolysis may be carried out in the presence of anisole. For the removal of the carboxyl-protecting group, a conventional deprotecting method such as hydrolysis or reduction can be applied. The hydrolysis with acid is one of the common deprotection techniques. It may be applied to for the removal of a carboxyl-protecting group such as silyl group or diphenylmethyl group. The saponification of the 2-carboxyl group may be effected by a manner known per se in the art.

The new compound of the formula (I) according to this invention may be formulated into a pharmaceutical composition by mixing with a pharmaceutically acceptable solid or liquid carrier or vehicle when it is to be administered to man for the therapeutic treatment of bacterial infections.

According to a further aspect of this invention, therefore, there is provided a pharmaceutical, antibacterial composition which comprises an antibacterially effective amount of the compound of the formula (I) as the active ingredient, in combination of a pharmaceutically acceptable carrier for the active ingredient.

The pharmaceutically acceptable carrier as mixed with the active ingredient compound may be an ordinary solid or liquid one, either organic or inorganic, which may be chosen appropriately depending on whether the pharmaceutical formulation as prepared is to be administered orally or non-orally or applied eternally. The pharmaceutical composition of this invention may be of any conventional formulation form such as capsules, tablets, sugar-coated pills, ointment, suppository, solution, suspension and emulsion. Other conventional additives, including adjuvant, stabilizing agent, wetting agent, emulsifying agent, buffer solution may also be incorporated into the pharmaceutical composition of this invention containing the compound (I) as the active ingredient.

The new cephalosporin compound of this invention as orally administered is easily absorbed through the intestines by a living animal and maintains its antibacterial activity to a substantial extent in the body of the animal until it is excreted in the urine of the animal, and this may be observed by determining the remaining amount of the cephalosporin compound of this invention which can be recovered in the urine without receiving a substantial degradation of the compound in vivo.

The production of some compounds of the formula (I) according to this invention is now illustrated with reference to the following Examples. Further, the preparation of certain starting compounds will also be illustrated in Referential Examples.

EXAMPLE 1

In N,N-dimethylformamide (8 ml) was dissolved sodium 7-[2-methoxyimino-2-(2-aminothiazol-4-yl)acetamido]-3-[2-(4-methylthiazol-5-yl)vinyl]-3-cephem-4-carboxylate (syn-isomer, cis-isomer) (1.06 g), followed by addition of bromomethyl acetate (612 mg) under ice-cooling. The reaction mixture was stirred for 30 minutes at the same temperature under ice-cooling. Ethyl acetate (50 ml) was then added to the reaction mixture. The resultant mixture was washed three times with 30 ml-portions of ice water and then with saline. Thereafter, the mixture thus washed was dried over magnesium sulfate. The ethyl acetate was distilled off under reduced pressure and the residue was dissolved in a small amount of methylene chloride.

The resultant solution was then purified by flash column chromatography on a column of "Wako Gel C-300" (trade name, product of Wako Pure Chemical Industries, Ltd.; 35 g) (eluant: mixed solvent of methylene chloride and acetone, 3:2). Fractions containing the intended product were combined together, followed by concentration to a small volume (about 2 ml) under reduced pressure. The concentrate was gradually added dropwise to hexane (about 20 ml) and the resultant precipitate was collected by filtration. After washing the precipitate with hexane, it was dried under reduced pressure to obtain 330 mg of acetoxymethyl 7-[2-methoxyimino-2-(2-aminothiazol-4-yl)acetamido]-3-[2-(4-methylthiazol-5-yl)vinyl]-3-cephem-4-carboxylate (syn-isomer, cis-isomer) as pale yellow powder (yield: 28%).

NMR (90 MHz, CDCl$_3$): 2.03 (3H, s), 2.43 (3H, s), 3.25 (1H, d, J=18 Hz), 3.53 (1H, d, J=18 Hz), 4.01 (3H, s), 5.16 (1H, d, J=5 Hz), 5.35 (2H, br-s), 5.73 (1H, d, J=5 Hz), 5.82 (1H, d, J=5 Hz), 6.03 (1H, d-d, J=5 Hz, 9 Hz), 6.31 (1H, d, J=12 Hz), 6.65 (1H, d, J=12 Hz), 6.82 (1H, s), 7.54 (1H, d, J=9 Hz), 8.56 (1H, s).

EXAMPLE 2

The procedures of Example 1 were repeated except for the use of α-bromoethyl acetate (670 mg) in lieu of the bromomethyl acetate. Thereby, 295 mg of 1-acetoxyethyl 7-[2-methoxyimino 2-(2-aminothiazol-4-yl)acetamido]-3-[2-(4-methylthiazol-5-yl)vinyl]-3-cephem-4-carboxylate was afforded as pale yellow powder (syn-isomer, cis-isomer) (yield: 25%). According to an NMR spectrum, the ester product obtained was a mixture of two isomers (as produced at ratio=1:1) due to the presence of the asymmetric carbon atom in the ester moiety.

NMR (90 MHz, CDCl$_3$): 1.42 (3/2H, d, J=5 Hz), 1.48 (3/2H, d, J=5 Hz), 1.98 (3/2H, s), 2.01 (3/2H, s), 2.41 (3H, s), 3.23 (1H, d, J=18 Hz), 3.51 (1H, d, J=18 Hz), 4.00 (3H, s), 5.15 (1H, d, J=5 Hz), 5.45 (2H, br-s), 6.04 (1H, d-d, J=5 Hz, 9 Hz), 6.31 (½H, d, J=12 Hz), 6.35 (½H, d, J=12 Hz), 6.61 (½H, d, J=12 Hz), 6.65 (½H, d, J=12 Hz), 6.79 (1H, s), 6.80–7.00 (1H, m), 7.74 (1H, d, J=9 Hz), 8.53 (1H, s).

EXAMPLE 3

The procedures of Example 1 were repeated except for the use of α-iodoethylethyl carbonate prepared from α-chloroethylethyl carbonate (1.53 g), instead of the bromomethyl acetate. Thereby 215 mg of α-ethoxycarbonyloxyethyl 7-[2-methoxyimino-2-(2-aminothiazol-4-yl)acetamido]-3-[2-(4-methylthiazol-5-yl)vinyl]-3-cephem-4-carboxylate was afforded as pale yellow powder (syn-isomer, cis-isomer) (yield: 17%). According to an NMR spectrum, the ester product obtained was a mixture of two isomers (as produced at ratio=1:1) due to the presence of the asymmetric carbon atom in the ester moiety.

NMR (400 MHz, CDCl$_3$): 1.29 (3/2H, t, J=7 Hz), 1.30 (3/2H, t, J=7 Hz), 1.49 (3/2H, d, J=6 Hz), 1.55 (3/2H, d, J=6 Hz), 2.44 (3/2H, s), 2.45 (3/2H, s), 3.32 (1H, d, J=19 Hz), 3.51 (1H, br-d, J=19 Hz), 4.05 (3H, s), 4.10–4.30 (2H, m), 5.20 (1H, br-d, J=5 Hz), 5.47 (2H, br-s), 6.07 (½H, d-d, J=5 Hz, 9 Hz), 6.09 (½H, d-d, J=5 Hz, 9 Hz), 6.38 (½H, d, J=12 Hz), 6.43 (½H, d, J=12 Hz), 6.66 (½H, d, J=12 Hz), 6.70 (½H, d, J=12 Hz), 6.85 (½H, q, J=6 Hz), 6.86 (1H, s), 6.91 (½H, q, J=6 Hz), 7.65 (1H, br-d, J=9 Hz), 8.65 (1H, s).

EXAMPLE 4

In dimethyl sulfoxide (8 ml) was dissolved sodium 7-[2-methoxyimino-2-(2-aminothiazol-4-yl)acetamido]-3-2-(4-methylthiazol-5-yl)vinyl]-3-cephem-4-carboxylate (syn-isomer, cis-isomer) (1.06 g), followed by addition of bromophthalide (640 mg). After stirring the resultant mixture at room temperature for 10 minutes, 30 ml of ice water was poured to terminate the reaction. The resultant precipitate was collected by filtration, and after washing it with water, the precipitate was dried under reduced pressure.

The dried precipitate was dissolved in methylene chloride and the solution was then purified by flash column-chromatography on a column of "Wako Gel C-300" (trade name, product of Wako Pure Chemical Industries, Ltd.; 35 g) (eluant: mixed solvent of methylene chloride and acetone, 3:2). Fractions containing the intended product were combined together, followed by concentration under reduced pressure. Diisopropyl ether (20 ml) was added to the residue and after thorough stirring, the resultant mixture was filtered to collect the resultant precipitate. The precipitate was then dried to give 710 mg of phthalidyl 7-[2-methoxyimino-2-(2-aminothiazol-4-yl)acetamido]-3-[2-(4-methyl-thiazol-5-yl)vinyl]-3-cephem-4-carboxylate (syn-isomer, cis-isomer) as powder of pale yellow color (yield: 55%). According to an NMR spectrum, the ester was a 1:1 mixture of the diastereomers.

NMR (400 MHz, CDCl$_3$): 2.40 (3/2H, s), 2.43 (3/2H, s), 3.32 (½H, d, J=19 Hz), 3.36 (½H, d, J=19 Hz), 3.55 (½H, d, J=19 Hz), 3.56 (½H, d, J=10 Hz), 4.00 (3/2H, s), 4.02 (3/2H, s), 5.15 (½H, d, J=5 Hz), 5.22 (½H, d, J=5 Hz), 5.36 (1H, br-s), 5.42 (1H, br-s), 6.03 (½H, d-d, J=5 Hz, 9 Hz), 6.09 (½H, d-d, J=5 Hz, 9 Hz), 6.25 (½H, d, J=12 Hz), 6.47 (½H, d, J=12 Hz), 6.64 (½H, d, J=12 Hz), 6.73 (½H, d, J=12 Hz), 6.84 (½H, s), 6.89 (½H, s), 7.4–7.9 (5H, m), 8.50 (½H, s), 8.55 (½H, s).

EXAMPLE 5

The procedures of Example 4 were repeated except for the use of 4-bromomethyl-5-methyl-2-oxo-1,3-dioxolene, which had been prepared from 300 mg of 4,5-dimethyl-2-oxo-1,3-dioxolene and 465 mg of NBS, instead of the bromophtalide. Thus, 910 mg of 5-methyl-2-oxo-1,3-dioxolene-4-ylmethyl 7-[2-methoxyimino-2-(2-aminothiazol-4-yl)acetamido]-3-[2-(4-methylthiazol-5-yl)vinyl]-3-cephem-4-carboxylate was obtained as pale yellow powder (syn-isomer, cis-isomer) (yield: 73%).

NMR (90 MHz, CDCl$_3$): 2.10 (3H, s), 2.43 (3H, s), 3.25 (1H, d, J=19 Hz), 3.54 (1H, d, J=19 Hz), 4.00 (3H, s), 4.76 (1H, d, J=14 Hz), 5.03 (1H, d, J=14 Hz), 5.18 (1H, d, J=5 Hz), 5.54 (2H, br-s), 6.19 (1H, d-d, J=5 Hz, 9Hz), 6.27 (1H, d, J=12 Hz), 6.63 (1H, d, J=12 Hz), 6.72 (1H, s), 7.95 (1H, br-d, J=9 Hz), 8.55 (1H, s).

EXAMPLE 6

Sodium 7-[2-ethoxyimino-2-(2-aminothiazol-4-yl)-acetamido]-3-[2-(4-methylthiazol-5-yl)vinyl]-3-cephem-4-carboxylate (syn-isomer, cis-isomer) (300 mg) was dissolved in N,N-dimethylformamide (3 ml), followed by addition of iodomethyl pivalate (270 mg) under ice-cooling. At the same temperature, the reaction mixture was stirred for 90 minutes. The reaction mixture was then diluted with 25 ml of ethyl acetate. After washed with ice water and then with saline, the reaction mixture was dried over magnesium sulfate. The solvent was distilled off under reduced pressure.

The residue was purified by flash column chromatography on a column of "Wako Gel C-300" (trade neme, product of Wako Pure Chemical Industries, Ltd.; 20 g) (eluant: ethyl acetate). Fractions containing the intended product were collected together and concentrated under reduced pressure. The residue was then taken up in methanol (about 2 ml). The resulting methanol solution was added dropwise to ice water (about 20 ml) and the precipitate as formed was collected by filtration. The precipitate was teen dried under reduced pressure to obtain 210 mg of pivaloyloxymethyl 7-[2-ethoxyimino-2-(2-aminothiazol-4-yl) acetamido]-3-[2-(4-methylthiazol-5-yl)vinyl]-3-cephem-4carboxylate (syn-isomer, cis-isomer) as pale yellow powder (yield: 60%).

NMR (90 MHz, CDCl$_3$): 1.13 (9H, s), 1.31 (3H, t, J=7 Hz), 2.42 (3H, s), 3.27 (1H, d, J=19 Hz), 3.58 (1H, d, J=19 Hz), 4.31 (2H, q, J=7 Hz), 5.16 (1H, d, J=5 Hz), 5.31 (2H, br-s), 5.77 (1H, d, J=5 Hz), 5.85 (1H, d, J=5 Hz), 6.04 (1H, d-d, J=5 Hz, 9 Hz), 6.32 (1H, d, J=12 Hz), 6.68 (1H, d, J=12 Hz), 6.88 (1H, s), 7.29 (1H, br-d, J=9 Hz), 8.57 (12H, s).

REFERENTIAL EXAMPLE 1

(a) In 50 ml of acetone were dissolved diphenylmethyl 7-phenylacetamido-3-chloromethyl-3-cephem-4-carboxylate (5.33 g, 10 mmoles), triphenylphosphine (2.62 g) and sodium iodide (1.5 g), and the solution was stirred at room temperature for 3 hours. The acetone was distilled off under reduced pressure. After dissolving the residue in a mixture of methylene chloride (70 ml) and water (30 ml), the resulting solution was admixed with 4-methylthiazole-5-carboaldehyde (6.35 g), followed by addition of sodium carbonate to adjust the pH of the reaction mixture to 9.0. The reaction mixture, which had separated into two phases, was stirred at room temperature for 1.5 hours. The organic layer was separated and then washed with saline. After drying the organic solution over magnesium sulfate, the solvent was distilled off under reduced pressure to leave an oily product of a dark red color. The oil was diluted with about 20 ml of benzene, followed by purification on a column of "Wako Gel C-30" (trade name, product of Wako Pure Chemical Industries, Ltd.; 400 g) (eluant: mixture of benzene and ethyl acetate, 3:1).

Fractions containing the intended product were collected together and concentrated under reduced pressure, to afford 2.07 g of diphenylmethyl 7-phenylacetamido-3-[2-(4-methylthiazol-5-yl)vinyl]-3-cephem-4-carboxylate as yellowish amorphous solid (yield: 34%).

NMR (90 MHz, CDCl$_3$): 2.33 (3H, s), 3.15 (1H, d, J=18 Hz), 3.50 (1H, d, J=18 Hz), 3.61 (2H, s), 5.05 (1H, d, J=5 Hz), 5.88 (1H, d-d, J=5 Hz, 9 Hz), 6.21 (1H, d, J=12 Hz), 6.48 (1H, d, J=12 Hz), 6.81 (1H, s), 7.20–7.40 (16H, m), 8.51 (1H, s).

(b) In 40 ml of methylene chloride was dissolved the diphenylmethyl 7-phenylacetamido-3-[2-(4-methylthiazol-5-yl)vinyl]-3-cephem-4-carboxylate (3.04 g, 5 mmoles) obtained as above. The resultant solution was cooled down to −20° C. After adding pyridine (1.62 ml) and phosphorus pentachloride (2.08 g), the resultant mixture was stirred at 5° C. for 3 hours and then cooled again to −20° C. After a prompt addition of 4 ml of methanol, the resultant mixture was stirred at 20° C. for 2 hours. The reaction mixture was then cooled to −10° C., followed by addition of 20 ml of chilled water. The mixture obtained was agitated vigorously. An aqueous solution of sodium bicarbonate was added to the mixture to adjust its pH to 2.0. The organic layer was then separated, followed by its washing with an aqueous solution of sodium bicarbonate and then with saline. The organic solution was then dried magnesium sulfate and the solvent was distilled off under reduced pressure. Ethyl acetate (10 ml) was added to the residue and the resultant mixture was allowed to stand overnight in an ice box. Deposited crystals were collected by filtration, washed with ethyl acetate and then dried under reduced pressure, to give 1.34 g of diphenylmethyl 7-amino-3-[2-(4-methylthiazol-5-yl)vinyl]-3-cephem-4carboxylate as yellow powder (yield: 54%).

NMR (90 MHz, CDCl$_3$): 1.72 (2H, br-s), 2.34 (3H, s), 3.20 (1H, d, J=18 Hz), 3.52 (1H, d, J=18 Hz), 4.79 (1H, d, J=5 Hz), 5.02 (1H, d, J=5 Hz), 6.21 (1H, d, J=12 Hz), 6.45 (1H, d, J=12 Hz), 6.86 (1H, s), 7.20–7.40 (10H, m), 8.52 (1H, s).

(c) In 5 ml of methylene chloride were suspended 2-(2-tritylaminothiazol-4-yl)-2-methoxyiminoacetic acid (syn-isomer) (467 mg) and 1-hydroxybenzotriazole monohydrate (161 mg). The resultant suspension was ice-cooled. N,N'-dicyclohexylcarbodiimide (217 mg) was added. Thirty minutes later, diphenylmethyl 7-amino-3-[2-(4-methylthiazol-5-yl)vinyl]-3-cephem-4-carboxylate (490 mg) obtained in the above procedure (b) was added further. The reaction mixture was then stirred for 4 hours under ice-cooling. After adding magnesium sulfate (500 mg) to the reaction mixture and then stirring the resultant mixture for 5 minutes, the reaction mixture was filtered. The solid matter was washed with methylene chloride. The filtrate and washing were combined together, followed by concentration under reduced pressure to obtain a foamed product of a dark red color. The foamed product was dissolved in a mixture of methylene chloride (2 ml), anisole (1 ml) and trifluoroacetic acid (6 ml). The resultant solution was then left over for 3 hours under ice-cooling. The solvents were mostly distilled off under reduced pressure, followed by addition of 20 ml of diisopropyl ether. The resulting precipitate was collected by filtration, washed with diisopropyl ether, and then dried under reduced pressure. The precipitate was suspended in 3 ml of chilled water, followed by addition of sodium bicarbonate to pH 8.5. When the suspension was stirred for 30 minutes under ice cooling, a cloudy solution of a red color was obtained. The solution was passed through a column of "DIAION HP-20" (trade name, absorbent resin product of Mitsubishi Chemical Industries, Ltd.; 20 ml). After washing the column with 50 ml of water in advance, the column was eluted with 30% methanol. Fractions containing the intended product were collected together, concentrated to about 3 ml under reduced pressure, and then lyophilized, to obtain 315 mg of sodium 7-[2-(2-aminothiazol-4-yl)-3-methoxyiminoacetamido-]-3-[2-(2-methylthiazol-5-yl)vinyl-3-cephem-4-carboxylate (syn-isomer, cis-isomer) as pale yellow powder (yield: 59%).

NMR (90 MHz, $D_2O$): 2.38 (3H, s), 3.29 (1H, d, J=18 Hz), 3.59 (1H, d, J=18 Hz), 3.99 (3H, s), 5.34 (1H, d, J=5 Hz), 5.83 (1H, d, J=5 Hz), 6.30 (1H, d, J=12 Hz), 6.65 (1H, d, J=12 Hz), 6.99 (1H, s), 8.75 (1H, s).

REFERENTIAL EXAMPLE 2

The procedures of Referential Example 1 were repeated except that 2-(2-tritylaminothiazol-4-yl)-2-ethoxyiminoacetic acid (syn-isomer) (482 mg) was used in place of the 2-(2-tritylaminothiazol-4-yl)-2-methoxyiminoacetic acid in the step (c) of Referential Example 1. Thus, 290 mg of sodium 7-[2-(2-aminothiazol-4-yl)-2-ethoxyiminoacetamido-]-3-[2-(4-methylthiazol-5-yl)vinyl]-3-cephem-4-carboxylate (syn-isomer, cis-isomer) was obtained as pale yellow powder (yield: 53%).

NMR (90 MHz, $D_2O$): 1.28 (3H, t, J=7 Hz), 2.36 (3H, s), 3.26 (1H, d, J=18 Hz), 3.57 (1H, d, J=18 Hz), 4.25 (2H, q, J=7 Hz), 5.32 (1H, d, J=5 Hz), 5.82 (1H, d, J=5 Hz), 6.28 (1H, d, J=12 Hz), 6.62 (1H, d, J=12 Hz), 6.95 (1H, s), 8.72 (1H, s).

Having now fully described the invention, it will be apparent to one of ordinary skill in the art that many changes and modifications can be made thereto without departing from the spirit or scope of the invention as set forth herein.

We claim:

1. The syn-isomer of a cephem compound represented by the following formula (I)

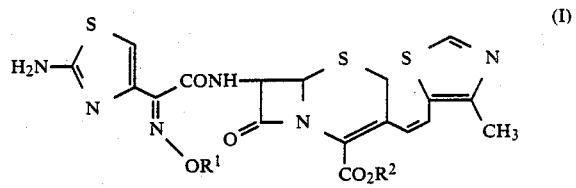

wherein $R^1$ means a lower alkyl group, $R^2$ denotes a lower alkanoyloxyalkyl group, a lower alkoxycarbonyloxyalkyl group, phthalidyl group or (5-methyl-2-oxo-1,3-dioxolen-4-yl)methyl group of the carboxyl group, and the 4-methylthiazolyl group and the cephem moiety are cis to each other relative to the carbon-carbon double bond of the substituted vinyl group in the side chain at the 3-position of the cephem nucleus.

2. The compound as claimed in claim 1, wherein $R^1$ is a methyl or ethyl group, and $R^2$ is a pivaloyloxymethyl, acetoxymethyl, 1-acetoxyethyl, 1-ethoxycarbonyloxyethyl, phthalidyl or (5-methyl-2-oxo-1,3-dioxolen-4-yl)methyl group.

3. The compound as claimed in claim 2, which is pivaloyloxymethyl 7-[2-ethoxyimino-2-(2-aminothiazol-4yl)acetamido-]-3-[2-(4-methylthiazol-5-yl)vinyl]-3-cephem-4-carboxylate.

4. The compound as claimed in claim 2, which is acetoxymethyl 7-[2-methoxyimino-2-(2-aminothiazol-4-yl)acetamido]-3-[2-(4-methylthiazol-5-yl)vinyl]-3-cephem-4-carboxylate.

5. The compound as claimed in claim 2, which is 1-acetoxyethyl 7-[2-methoxyimino-2-(2-aminothiazol-4-yl)acetamido-]-3-[2-(4-methylthiazol-5-yl)vinyl]-3-cephem-4-carboxylate.

6. The compound as claimed in claim 2, which is 1-ethoxycarbonyloxyethyl 7-[2-methoxyimino-2-(2-aminothiazol-4-yl)acetamido]-3-[2-(4-methylthiazol-5-yl)vinyl]-3-cephem-4-carboxylate.

7. The compound as claimed in claim 2, which is phthalidyl 7-[2-methoxyimino-2-(2-aminothiazol-4-yl)acetamido]-3-[2-(4-methylthiazol-5-yl)vinyl]-3-cephem-4-carboxylate.

8. The compound as claimed in claim 2, which is (5-methyl-2-oxo-1,3-dioxolen-4-yl)methyl 7-[2-methoxyimino-2-(2-aminothiazol-4-yl)acetamido]-3-[2-(4-methylthiazol-5-yl)vinyl]-3-cephem-4-carboxylate.

9. A pharmaceutical, antibacterial composition which comprises an antibacterially effective amount compound of the formula (I) as defined in claim 1 as the active ingredient, in combination with a pharmaceutically acceptable carrier for the active ingredient.

* * * * *